United States Patent [19]

Bailey

[11] Plant 4,853

[45] Jun. 1, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,249

[22] Filed: Sep. 8, 1980

[51] Int. Cl.[3] ..... A01H 5/00

[52] U.S. Cl. ..... Plt./11

[58] Field of Search ..... Plt./11

*Primary Examiner*—James R. Feyrer

*Attorney, Agent, or Firm*—Vincent G. Gioia

[57] ABSTRACT

A new hybrid tea rose variety of exhibition form and orange red and cadmium yellow.

1 Drawing Figure

1

The present invention relates to a new and distinct variety of rose plant of the hybrid tea rose class, which was originated by my crossing as seed parent the rose known as "Kordes Perfecta" and the rose known as "Mr. Lincoln" as pollen parent.

Among the novel characteristics possessed by this new variety which distinguish it from its parents and all other varieties of which I am aware are its excellent exhibition form and unusual cadmium yellow and orange red coloring at the bottom and top petal edge surfaces, respectively. The flowers are borne primarily singly on a plant with abundant foliage and superior disease resistance. Asexual reproduction by budding of the new variety as performed in Kern County, Calif., shows that the foregoing and other distinguishing characteristics come true to form and are established and transmitted through succeeding propagations.

The new and improved rose variety which I have developed is a fine hybrid tea rose with unusual coloring, of high centered, excellent hybrid-tea form displayed on a vigorous, free branching plant with abundant disease resistant foliage. The flowers are of heavy petalage and have a slight fragrance.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "23D" is plate 23D of the Royal Horticultural Society Color Chart.

Parentage: Seedling.

*Seed parent.*—"Kordes Perfecta".

*Pollen parent.*—"Mr. Lincoln".

Class: Hybrid tea.

The following observations are made of specimens grown outdoors in Kern County, Calif., during the month of October.

1. FLOWER

Blooming habit: Recurrent.

A. Bud:

(1) *Size.*—Large.

(2) *Form.*—Long pointed.

2

(3) *Color.*—First row of petals in bud after sepals fall show petal undersurface color cadmium orange 23D, slightly darker at petal point of attachment. At under surface petal edge, color is between 34D and 37A with color intensity greatest at the lateral edges.

(4) *Sepals.*—Simple, about same length as bud.

(5) *Peduncle.*—Length — about 4 inches. Aspect — straight, smooth. Strength — erect, strong. Color — near 146B with purplish red cast.

B. Bloom:

(1) *Size.*—Average size when fully expanded — about $4\frac{1}{2}$ to 5 inches.

(2) *Borne.*—Primarily singly.

(3) *Form.*—High centered, petals recurve, maintain high centered exhibition form with circular outline.

(4) *Petalage.*—Number of petals under normal conditions — about 48 to 50.

(5) *Color.*—As flowers open petal undersurface color 23D remains about the same and orange red coloring (between 34D and 37A) at petal edges on top surface becomes more prominent but dual coloring of individual petals is also evident on the top petal surface. The washing of the darker orange red coloring at the edging into the cadmium orange, which also appears to lighten on inner petals, makes the petal veining more visible. In the open bloom there is varied orange red to red (39A) coloring most visible on the petal edges and highlights of 39C and 39D may be seen.

C. Petals:

(1) *Texture.*—Thick, good substance.

(2) *Appearance.*—Velvety to satiny.

(3) *Form.*—Rounded.

(4) *Arrangement.*—Regularly arranged.

(5) *Petaloids in center.*—Few.

(6) *Persistence.*—Drop off cleanly.

(7) *Fragrance.*—Slight.

(8) *Lasting quality.*—Long lasting on plant and as cut flower.

2. REPRODUCTIVE ORGANS

A. Stamens, filaments and anthers:

(1) *Arrangement.*—Regularly arranged about styles.

(2) *Color.*—26B.

B. Pollen:

*Color.*—23B.

C. Styles: Uniform and long.
D. Stigmas:
*Color.*—31B.
E. Hips:
*Shape.*—Globular.
*Size.*—Large.
*Color.*—25A.
*Do seeds protrude?*—Slightly.

3. PLANT

A. Form: Upright.
B. Growth: Vigorous.
*Height attained.*—About 4½ feet first season.
C. Foliage: Compound 5 to 7 leaflets.
(1) *Size.*—Large.
(2) *Quantity.*—Abundant.
(3) *Color.*—New foliage: upper side — purplish red; under side — greenish red. Old foliage: upper side — near 136A to 136B; under side — near 191A.
(4) *Shape.*—Oval.
(5) *Texture.*—Upper side is leathery and under side is dull.
(6) *Edge.*—Serrated.
(7) *Serration.*—Simple.

(8) *Leaf stem.*—Color — near to 146B. Under side — near 147C.
(9) *Stipules.*—Long, slightly bearded.
(10) *Resistance to disease.*—Blackspot — excellent. Mildew — excellent.
D. Wood:
(1) *New wood.*—Color — near 146B with red tones. Bark — smooth.
(2) *Old wood.*—Color — near 146A. Bark — smooth.
E. Thorns:
(1) *Thorns.*—Quantity (main stalk) — few. On laterals from stalk — very few. Form — ovoid. Length — large. Color — near 146C. Position — regular.
(2) *Prickles.*—None.
F. Winter hardiness: Good winter hardiness.

I claim:

1. A new and distinct variety of rose plant of the hybrid tea class, substantially as shown and described, characterized particularly by high centered, flowers of good exhibition form and cadmium yellow petals with orange red petal edges borne primarily singly to a stem.

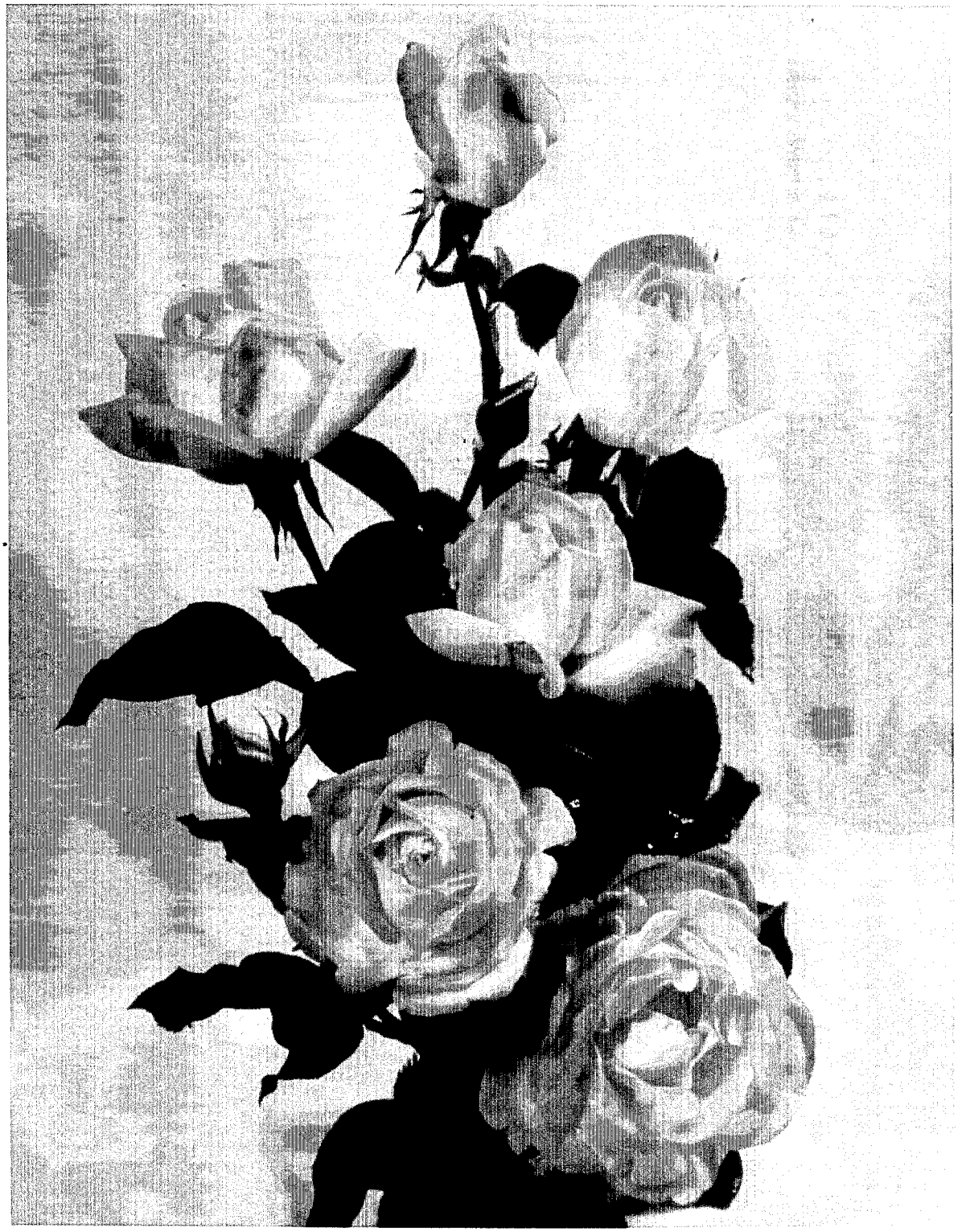

* * * * *